(12) United States Patent
Delattre et al.

(10) Patent No.: US 10,252,065 B2
(45) Date of Patent: Apr. 9, 2019

(54) PULSE GENERATING SYSTEM

(71) Applicant: GTX medical B.V., Eindhoven (NL)

(72) Inventors: Vincent Delattre, Eindhoven (NL); Joachim Von Zitzewitz, Eindhoven (NL); Sjaak Deckers, Eindhoven (NL)

(73) Assignee: GTX medical B.V., Eindhoven (NL)

( * ) Notice: Subject to any disclaimer, the term of this patent is extended or adjusted under 35 U.S.C. 154(b) by 0 days.

(21) Appl. No.: 15/649,524

(22) Filed: Jul. 13, 2017

(65) Prior Publication Data
US 2018/0015292 A1    Jan. 18, 2018

(30) Foreign Application Priority Data
Jul. 15, 2016    (EP) ..................... 16001570

(51) Int. Cl.
*A61N 1/372*    (2006.01)
*A61N 1/36*    (2006.01)
*A61B 5/00*    (2006.01)
*A61B 5/0488*    (2006.01)
*A61N 1/39*    (2006.01)
*A61N 1/368*    (2006.01)
*A61N 1/37*    (2006.01)

(52) U.S. Cl.
CPC ........ *A61N 1/37235* (2013.01); *A61B 5/0031* (2013.01); *A61N 1/36071* (2013.01); *A61N 1/3688* (2013.01); *A61N 1/372* (2013.01); *A61N 1/3718* (2013.01); *A61N 1/3931* (2013.01); *A61B 5/0488* (2013.01)

(58) Field of Classification Search
None
See application file for complete search history.

(56) References Cited

U.S. PATENT DOCUMENTS

| 5,571,141 A | 11/1996 | McNeil et al. |
| 6,188,927 B1 | 2/2001 | Lu et al. |
| 6,516,227 B1 * | 2/2003 | Meadows ............ A61N 1/0553 607/117 |

(Continued)

FOREIGN PATENT DOCUMENTS

| EP | 2868343 A1 | 5/2015 |
| WO | 2007047852 A2 | 4/2007 |

OTHER PUBLICATIONS

Guyatt, G. et al., "The 6-minute walk: a new measure of exercise capacity in patients with chronic heart failure," Canadian Medical Association Journal, vol. 132, No. 8, Apr. 15, 1985, 5 pages.

(Continued)

*Primary Examiner* — Brian T Gedeon
(74) *Attorney, Agent, or Firm* — McCoy Russell LLP

(57) ABSTRACT

The present disclosure relates to a pulse generating system comprising a pulse generator for generating a pulse or pulses and a controller for controlling the pulse generating means, where the pulse generating system is capable to work in at least a regular mode and a safety mode, where in the regular mode the pulse generator and the controller are connected and where in the safety mode there is no connection between the pulse generator and the controller and where in the safety mode the pulse generator automatically switches to a baseline stimulation command.

20 Claims, 3 Drawing Sheets

(56) References Cited

U.S. PATENT DOCUMENTS

| | | | | |
|---|---|---|---|---|
| 7,769,464 | B2* | 8/2010 | Gerber | A61N 1/36514 |
| | | | | 607/59 |
| 7,813,809 | B2 | 10/2010 | Strother et al. | |
| 9,592,385 | B2* | 3/2017 | Kaula | A61N 1/36132 |
| 2007/0004567 | A1 | 1/2007 | Shetty et al. | |
| 2015/0057717 | A1* | 2/2015 | Wu | A61N 1/37235 |
| | | | | 607/30 |

OTHER PUBLICATIONS

Lovely, R. et al., "Effects of Training on the Recovery of Full-Weight-Bearing Stepping in the Adult Spinal Cat," Experimental Neurology, vol. 92, No. 2, May 1986, 15 pages.

Barbeau, H. et al., "Recovery of locomotion after chronic spinalization in the adult cat," Brain Research, vol. 412, No. 1, May 26, 1987, 12 pages.

Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.

Wernig, A. et al., "Laufband locomotion with body weight support improved walking in persons with severe spinal cord injuries," Paraplegia, vol. 30, No. 4, Apr. 1992, 10 pages.

Winter, D. et al., "An integrated EMG/biomechanical model of upper body balance and posture during human gait," Progress in Brain Research, vol. 97, Chapter 32, Available as Early as Jan. 1, 1993, 9 pages.

Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.

Pratt, G. et al., "Stiffness Isn't Everything," Proceedings of the Fourth International Symposium on Experimental Robotics (ISER '95), Jun. 30, 1995, Stanford, California, 6 pages.

Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.

Harkema, S. et al., "Human Lumbosacral Spinal Cord Interprets Loading During Stepping," Journal of Neurophysiology, vol. 77, No. 2, Feb. 1, 1997, 15 pages.

Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.

Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.

Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.

Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.

Pratt, J. et al., "Series elastic actuators for high fidelity force control," Industrial Robot: An International Journal, vol. 29, No. 3, Available as Early as Jan. 1, 2002, 13 pages.

Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.

Pearson, K., "Generating the walking gait: role of sensory feedback," Progress in Brain Research, vol. 143, Chapter 12, Published Online Nov. 28, 2003, 7 pages.

Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.

Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.

Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.

Wernig, A., "'Ineffectiveness' of Automated Locomotor Training," Archives of Physical Medicine and Rehabilitation, vol. 86, No. 12, Dec. 2005, 2 pages.

Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.

Reinkensmeyer, D. et al., "Tools for understanding and optimizing robotic gait training," Journal of Rehabilitation Research & Development, vol. 43, No. 5, Aug. 2006, 14 pages.

Frey, M. et al., "A Novel Mechatronic Body Weight Support System," IEEE Transactions on Neural Systems and Rehabilitation Engineering, vol. 14, No. 3, Sep. 18, 2006, 11 pages.

Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.

Courtine, G. et al., "Can experiments in nonhuman primates expedite the translation of treatments for spinal cord injury in humans?," Nature Medicine, vol. 13, No. 5, May 2007, 13 pages.

Drew, T. et al., "Cortical mechanisms involved in visuomotor coordination during precision walking," Brain Research Reviews, vol. 57, No. 1, Jan. 2008, Published Online Aug. 22, 2007, 13 pages.

Edgerton, V. et al., "Training Locomotor Networks," Brain Research Reviews, vol. 57, No. 1, Jan. 2008, Published Online Sep. 16, 2007, 25 pages.

Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.

Courtine, G. et al., "Recovery of supraspinal control of stepping via indirect propriospinal relay connections after spinal cord injury," Nature Medicine, vol. 14, No. 1, Jan. 6, 2008, 6 pages.

Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.

Vallery, H. et al., "Compliant Actuation of Rehabilitation Robots," IEEE Robotics & Automation Magazine, vol. 15, No. 3, Sep. 12, 2008, 10 pages.

Edgerton, V. et al., "Robotic Training and Spinal Cord Plasticity," Brain Research Bulletin, vol. 78, No. 1, Jan. 15, 2009, Published Online Nov. 14, 2008, 19 pages.

Fuentes, R. et al., "Spinal Cord Stimulation Restores Locomotion in Animal Models of Parkinson's Disease," Science, vol. 323, No. 5921, Mar. 20, 2009, 14 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.

Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.

(56) References Cited

OTHER PUBLICATIONS

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 10 pages.
Wenger, N. et al., "Spatiotemporal neuromodulation therapies engaging muscle synergies improve motor control after spinal cord injury," Nature Medicine, vol. 22, No. 2, Feb. 2016, Published Online Jan. 18, 2016, 33 pages.

* cited by examiner

PULSE GENERATING SYSTEM

CROSS REFERENCE TO RELATED APPLICATION

This application claims priority to European Patent Application No. 16001570.7, entitled "Pulse Generating System," filed Jul. 15, 2016, the entire contents of which are hereby incorporated by reference in its entirety for all purposes.

TECHNICAL FIELD

The present disclosure relates to a pulse generating system comprising a pulse generating means (e.g., pulse generator) for generating a pulse or pulses and a controlling means (e.g., controller) for controlling the pulse generating means.

BACKGROUND AND SUMMARY

Pulse generation systems are known from various medical applications, inter alia from neurostimulation applications and from pacemakers.

Also, such pulse generation systems are used in systems to deliver adaptive electrical spinal cord stimulation to facilitate and restore locomotion after neuromotor impairment as e.g. described in EP 2 868 343 A1.

U.S. Pat. No. 7,813,809 B2 describes an implantable pulse generator for prosthetic or therapeutic stimulation of muscles, nerves, or central nervous system tissue, or any combination is sized and configured to be implanted in subcutaneous tissue. The implantable pulse generator includes a case and a control circuitry located within the case, and includes a primary cell or rechargeable power source, a receive coil for receiving an RF magnetic field to recharge the rechargeable power source, non-inductive wireless telemetry circuitry, and a microcontroller for control of the implantable pulse generator.

U.S. Pat. No. 6,188,927 B1 discloses an implantable cardiac stimulation system, which automatically optimizes its ability to rate-responsively pace by enabling calibration when the patient is at rest and has a functioning lead. Devices, which employ physiologic sensors, are based on a baseline value of the sensor signal corresponding to the resting state. Accordingly, the control system determines if the patient is at rest using a suitable sensor and also determines if the lead impedance is within normal values, i.e. functional and intact. If these conditions are met, the control system stores the current baseline of the sensor at rest and proceeds with normal sensing and stimulation commands until the next calibration is performed. In addition, the system can automatically calibrate a sleep value for the physiologic sensor using a sensor which can detect the sleep state. While the preferred embodiment discloses a minute ventilation sensor, other closed-loop sensors are contemplated, including at least paced depolarization integral (PDI), QT interval and pre-ejection interval (PEP).

Furthermore, U.S. Pat. No. 5,571,141 describes implantable automatic cardioverter/defibrillator device for a cardiac patient has a primary control mode for a defibrillation therapy delivery system. The primary control mode is responsive to detection of fibrillation of the patient's heart for causing the delivery of a preselected electrical waveform therapy to the heart. The device also has a secondary control mode, which is enabled by detecting a predetermined failure mechanism that causes malfunctioning of the primary mode. The enabled secondary control mode uses at least some of the functional part of the primary mode in responding to fibrillation of the patient's heart to initiate generation of defibrillation therapy for application to the patient's heart.

In Wenger et al., spatiotemporal neuromodulation therapies engaging muscles synergies improve motor control after spinal cord injury, in: nature medicine, advanced online publication, published online Jan. 18, 2016, electrical neuromodulation of lumbar segments improvement of motor control after spinal cord injury in animal models and humans is described.

Furthermore, Wenger et al., Closed-loop neuromodulation of spinal sensorimotor circuits controls refined locomotion after complete spinal cord injury, in: www.ScienceTranslationalMedicine.org, Vol. 6, issue 255ra133 (2014), closing the loop on neuro prosthetic control, describes a closed-loop neuromodulation system of spinal sensory motor circuits.

It is an object of the present disclosure to provide a pulse generating system, which provides enhanced functionality, especially in that different operation modes can be provided, for example in the field of neurostimulation, here e.g. the field of stimulation of the spinal cord and especially in the field of recovery after neurological disorders and/or trauma.

The above object is obtained according to the present disclosure by, in one example, a pulse generating system including a pulse generator adapted to generate a pulse or pulses; and a controller adapted to control the implantable pulse generator, wherein the pulse generating system is adapted to operate in at least a regular mode and a safety mode, wherein in the regular mode the pulse generator and the controller are connected and wherein in the safety mode there is no or limited connection between the pulse generator and the controller and wherein in the safety mode the pulse generator automatically switches to a baseline stimulation command.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
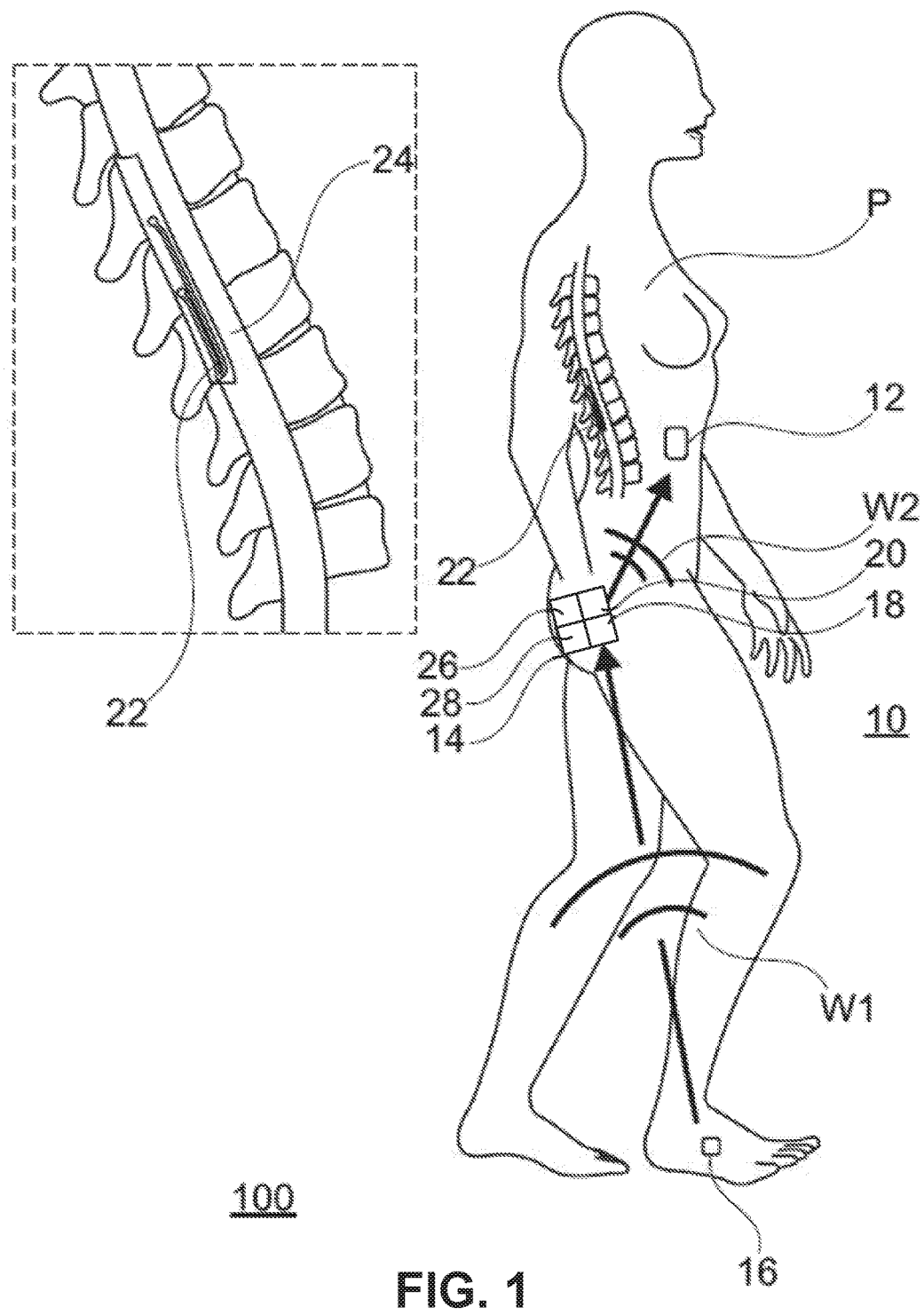
FIG. 1 shows an embodiment of a closed loop neurostimulation system.

The following description relates to systems and methods for a pulse generating system adapted to operate in two different stimulation modes based on the presence of electronic connections between components of the system and/or a position or movement of a patient in which the system is installed. FIG. 1 shows an embodiment of a pulse generating system including an implantable pulse generator (IPG) and a control unit (e.g., controller) which are electronically connected to one another via a wired or wireless connection. During operation, the system may automatically switch between a first operational mode where the control unit determines and sends control commands to the IPG for applying stimulation pulses to the patient and a second operational mode where the control unit and IPG may be disconnected and the IPG applies a baseline stimulation pulse to the patient instead of a pulse commanded by the control unit (which may be based on input from one or more sensors on the patient), as shown in the example method of FIG. 2. Examples of the different stimulation pulses applied to the patient via the IPG during the two operational modes are shown in FIG. 3.

The disclosure is based on the idea and concept that there shall be at least a regular mode and a safety mode and that it is possible to switch without any explicit command entered by the patient or user from one mode to the other and vice versa. Nevertheless, it shall he in general possible to enter also explicit, voluntary commands. However, in a case when the controlling means (e.g., controller or control unit) and the pulse generating means (e.g., implantable pulse generator or pulse generating device) lose for whatever reason the connection, at least the baseline stimulation command shall be provided. This design and functionality allows an improved functionality of the pulse generating system and increases the safety of the overall pulse generating system. By providing a baseline stimulation command in a situation, where there is no connection between the pulse generating means and the controlling means, it is guaranteed that the pulse generating means will not create and provide pulse or pulses on its own and thus respective stimulation commands that are unwanted. Consequently, the pulse generating system can only provide commands that are designed and adjusted for the respective purpose and there will be no commands without any control or the like. In other words, the pulse generating means may only generate pulse or pulses different from baseline stimulation, if the controlling means is capable to control the pulse generating means.

Moreover, the pulse generating means and the controlling means may be separated from each other. By this, it is possible, to exchange the pulse generating means or the controlling means separately from each other. This aspect may be beneficial after long-term implantations of the pulse generating system. Furthermore, the maintenance of the system is simplified. Additionally, by this modular approach the system design and architecture can be simplified. Also, several pulse generating means available on the market may be used, i.e. it is not necessary to focus only on one commercial available pulse generating means, but to use available pulse generating means that fit to the purpose.

The pulse generating means may be an implantable pulse generator (IPG). By this, existing IPGs may be used and thus, the realization and manufacturing of the pulse generating system is simplified. Moreover, regulatory affairs will be easier, as existing IPGs may already have FDA approval or the necessary CE-mark, which is needed for market entry in the respective countries.

In a further embodiment it is possible that the controlling means are controlling means of a neurostimulation system. In such a case the pulse generating means may generate the pulses for the neurostimulation and the controlling means may control or may be adapted to control the pulse generating means such that the planned neurostimulation can be provided. Especially, the neurostimulation system may be a system for stimulation of the spinal cord. Inter alia, the neurostimulation system may be a neurostimulation system for improving recovery after neurological disorders. Such a neurostimulation may be a neurostimulation for patients with spinal cord injury (SCI) and paralysis, which may electrically stimulate the brain and/or the spinal cord in order to enable or facilitate movement of the legs and arms, or to assist the patient in the voluntary control of standing and walking. In particular, the neurostimulation may be a neurostimulation of patients with neurological disorders affecting motor control of the lower limbs or upper limbs e.g. incomplete spinal cord injury. Additionally, the controlling means for controlling the pulse generating means may he connected with one or more sensors and may be forming a closed-loop system together with the sensors. By means of the sensors and the current control state and settings the controlling means may be adapted to modify and adjust the control signals based on the sensor input in order to control and provide the pulse generating means with the signals that are needed in the respective situation.

Such a control may be done within real-time. Real time means that based on the sensing the respective control and the providing of the necessary signals and stimulation pulses is done without delay or without significant delay, i.e. that sensing and stimulating is done in real-time or close to real-time. Close to real-time means that there is only a minimum delay. For example, it means that the delay is within a time frame of about 0.0 or 0.1 ms (milliseconds) and about 100.0 ms, especially within a time frame of about 0.01 ms and 90.0 ms, and, in another embodiment. within a time frame of about 5 ms and 35 ms.

In the regular mode the controlling means may be capable and configured to control the pulse generating means by providing control commands, especially control commands based on the sensor input by the at least one sensor. By this, the controlling of the pulse generating means by means of the controlling means can be adapted to the situation and performed in real-time or close to real-time.

The controlling means may be configured to control the pulse generating means with a one-way information flow, i.e. that the controlling means only sends signals and/or control commands to the pulse generating means.

It is, however, also possible that the controlling means is configured to control the pulse generating means with a two-way information flow. In particular, it is possible that the controlling means may be able to interact with the pulse generating means such that it not only sends but also receives information and/or signals from the pulse generating means. Such information and/or signals may be used to influence the control commands provided by the controlling means.

Moreover, the baseline stimulation command for the safety mode may be a default value set during a (baseline) parameterization session. Such a parameterization session can be done intra-operatively during the surgery, i.e. the implantation of the pulse generating system or parts of the pulse generating system. Alternatively, this can be also done post-operatively in a separate session. In other words, the baseline stimulation command may be set by qualified persons during a baseline parameterization session, in one embodiment, occurring after the implantation of the pulse generating system and the neurostimulation components.

Also, it is possible that the baseline stimulation command for the safety mode is set NULL by default. By a setting to NULL is a possible option to bring the whole pulse generating system in the safety mode into a safe state and to ensure this without the need of doing a baseline parameterization session. It is possible that both options are provided, i.e. a setting to NULL and the setting of a baseline stimulation command. In case that no baseline stimulation command is set or such a baseline stimulation command cannot be applied for whatever reason, then it is possible that the controlling means relies on the default value, which is NULL.

The baseline stimulation command may be also applied depending on the posture of the patient or the orientation of the patient.

Depending on a detected posture or orientation of the patient, the regular mode or the safety mode may be (automatically) chosen. In other words, the safety mode may be also linked to the patient orientation as triggering event or condition, which is used to decide between regular mode or safety mode. The patient orientation, e.g. whether the patient is standing or lying or sitting or the like, may be linked to a specific baseline command in the safety mode, i.e. there may he different sets of baseline commands for specific kinds of safety modes designed to fit to the posture or orientation of the patient. This enhances the overall safety of the system in ease that the patient changes from an active state, where the system is in the regular mode, like walking, tripping, falling to a resting state, where he is standing, lying or sitting and where the or one of the safety mode(s) is most suitable.

The pulse generating system may comprise an automatic switching unit, which is configured to switch automatically from the regular mode to the safety mode and vice versa. By means of this automatic switching unit the switching between a regular mode and a safety mode may be done very reliable. The automatic switching unit may be an electronic automatic switching unit.

The automatic switching unit may be configured to switch automatically from the regular mode to the safety mode, if a signal is received by the automatic switching unit, which indicates that the controlling means have determined that the most adapted stimulation command to be provided by the pulse generating means is the baseline stimulation command. Such a determination by the controlling means may he triggered by sensor input or simply by the fact that the patient makes no movement.

The automatic switching unit may be configured to switch automatically from regular mode to the safety mode, if a signal is received by the automatic switching unit, which indicates that the connection between the pulse generating means and the controlling means is lost. In such a situation, where there is no connection between the pulse generating means and the controlling means, i.e. that the pulse generating means may no longer be controlled by the controlling means, then it is from a safety perspective advisable to ensure that the pulse generating means cannot provide any pulse or pulses, which would then not be appropriate for the patient.

The automatic switching unit may be configured to switch automatically from safety mode to the regular mode, if a signal is received by the automatic switching unit, which indicates that the controlling means have determined that the most adapted stimulation command to be provided by the pulse generating means is the command different from the baseline stimulation command.

Such a situation may be for example indicated, when the patient begins to move. For example, this can happen when the patient wants to stand up from a lying position or a sitting position or when the patient is standing, but not moving. When for example by means of one sensor or sensors it is determined that the patient wants to move, the controlling means determine that now a signal or a command different from the baseline stimulation command is needed and may address the pulse generating means accordingly.

Also, the automatic switching unit may be configured to switch automatically from safety mode to the regular mode, if a signal is received by the automatic switching unit, which indicates that the connection between the pulse generating means and the controlling means is restored after it was lost. If so, it can he detected that the pulse generating system is again operative and that from the safe mode, here the safety mode the whole system may return to an operative mode, i.e. here the regular mode.

Additionally, the pulse generating system may comprise a user input switching unit to switch upon user input from the regular mode to the safety mode and vice versa. By this, voluntary control commands may be input by the user, for example by a patient or a medical practitioner like a nurse or a physician.

There may be a further and additional safety mode switching means, which are configured to switch the pulse generating system automatically from regular mode to safety mode triggered by technical system parameters. Such a parameter may be low power or low battery power RF signal interferences, detected noise signal or disturbing signals, intermittent contact or connection between components of the system like the connection between the controlling means and/or the pulse generating means and/or the sensor.

Moreover, the pulse generating system further comprises connection bridging means, which are configured to bridge the temporarily non-existing connection by replacing it with stored data, especially stored data obtained by simulation. If there is intermittent contact or connection between components of the system like the connection between the controlling means and/or the pulse generating means and/or the sensor, there may be connection bridging means. Such a connection bridging means may be capable to bridge the temporarily non-existing connection by replacing it with stored data or signal data. Such data may be derived from or based on simulation data derived from comparable situations. In particular, sensor data may be simulated or taken from comparable situations and stored in a suitable simulation sensor data storage means. The sensor input, which is not available in case of an intermittent contact or connection between components of the system like the connection between the controlling means and/or the pulse generating means and/or the sensor can then be replaced by the simulated sensor data in order to bridge the gap in the time frame, where there is no connection, e.g. between the sensor and the controlling means.

FIG. 1 shows a neurostimulation system, especially a closed-loop neurostimulation system 100 comprising a pulse generating system 10, as described above. Specifically, FIG. 1 shows a patient P with an implanted pulse generating system 10. In this way, the pulse generating system 10 is implanted into the patient P.

The pulse generating system 10 comprises a pulse generating means 12 for generating a pulse or pulses and a controlling means 14 for controlling the pulse generating means 12.

Furthermore, there is at least one sensor 16 attached to the patient P.

Additionally, the pulse generating system 10 comprises an automatic switching unit 18 and a user input switching unit 20. In one example, the automatic switching unit 18 and user input switching unit 20 may be a single unit included with a same casing (e.g., housing).

The pulse generating means 12 is connected to a lead 22 with electrodes 24.

The pulse generating system 10, including the pulse generating means 12 and the controlling means 14, the sensor 16, the automatic switching unit 18, the user input switching unit 20 and the lead 22 with electrodes 24 form the closed-loop neurostimulation system 100 for improving recovery after neurological disorders, i.e. to help the patient P to voluntary control locomotion after a spinal cord injury (SCI).

Generally speaking, the pulse generating system 10 may be also used and adapted for other neurostimulation treatments.

The pulse generating means 12 may be an implantable pulse generator (IPG).

As shown in the figure, the pulse generating means 12 and the controlling means 14 are separated from each other.

The pulse generating means 12 and at least parts of the controlling means 14 may be both implanted into the patient P.

It is also possible that the controlling means 14 are completely arranged outside of the body of the human patient P.

In the shown embodiment in FIG. 1, the controlling means 14 are arranged outside of the body of the patient.

Via wireless connection W1 the sensor 16 and the controlling means 14 are connected.

In the shown embodiment, the pulse generating means 12 and the controlling means 14 form separate modules. In an alternate embodiment, it is possible that the pulse generating means 12 and the controlling means 14 are arranged within in one housing (e.g., integrated within a single unit).

As shown, the pulse generating means 12 and the controlling means 14 are connected wirelessly to each other via wireless connection W2. In general, also a wired connection may be possible.

Also, at the same time a wireless connection and a wired connection may be possible.

Additionally, there is the array of electrodes 24 on the lead 22 that is connected with the pulse generating means 12. Here, the connection may be also wired or wireless.

The pulse generating system 10 further comprises a safety mode switching means (also referred to herein as a safety mode switching unit or safety mode switch) 26, which are configured to switch the pulse generating system 10 automatically from regular mode to safety mode triggered by technical system parameters. As described below, in one embodiment, the safety mode switching means 26 may be an electronic module or electronic switch that is connected to or part of the control unit 14.

Moreover, the pulse generating system 10 further comprises connection bridging means 28, which are configured to bridge the temporarily non-existing connection by replacing it with stored data, especially stored data obtained by simulation. As described below, in one embodiment, the connection bridging means 28 may be an electronic module that is connected to or part of the control unit 14 and may access data stored in a memory of the control unit 14. For example, the connection bridging means 28 may be an electronic connection bridging unit or connection bridge 28.

The functionality of the pulse generating system 10 can be described as follows:

The shown implantable neurostimulation system (INS), i.e. the implanted part of the closed-loop neurostimulation system 100, is composed of the IPG, i.e. the implanted pulse generating means 12, connected with the lead 22 and the electrical stimulation site or sites, here the electrodes 24, positioned in or over targeted neural structures, here the spinal cord, particularly in case of locomotion, above lumbo-sacral part of the spinal cord and in case of upper limb movements above the cervical part of the spinal cord.

The controller (e.g., control) unit, i.e. the controlling means 14, is an external device with an internal intelligence (i.e. software and processor unit) and which optionally provides a user interface for the implanted subject or for a third party person. Specifically, the control unit 14 may be coupled to various components of the neurostimulation system 100 to carry out the control routines and actions described herein (such as the control routine shown in FIG. 2, as described further below). For example, the control unit 14 may include a processor unit, input/output ports, an electronic storage medium for executable programs and calibration values, random access memory, keep alive memory, and/or a data bus. As depicted, the control unit 14 may receive input from a plurality of sensors, such as sensor 16. The control unit may also receive user inputs via additional wireless signals or connections. The control unit 14 may include one or more algorithms for analyzing the various signals received from sensor 16 and/or from received user inputs. Furthermore, control unit 14 may communicate with various components of the pulse generating system 10, which may include the pulse generating means (e.g., implantable pulse generator) 12. In some examples, the storage medium (e.g., memory) may be programmed with computer readable data representing instructions executable by the processor for performing the methods described below (with reference to FIG. 2) as well as other variants that are anticipated but not specifically listed. Additionally, in some embodiments, the control unit 14 includes multiple modules or units. For example, one or more of the safety mode switching means 26, the connection bridging means 28, the user input switching means 20, and the automatic switching unit 18 may be modules or units contained within or electronically coupled to the control unit 14.

The control unit 14 receives information via wireless connection W1 from the sensors, here sensor 16.

In the regular function mode the IPG 12 and the control unit 14 are connected, which through physical or through telemetric connection, here wireless connection W2, and the control unit 14 communicates stimulation commands to the IPG 12.

Multiple sets of stimulation commands can be defined from multitude of defined tasks and stored in the system 10. The control unit 14 receives sensor input, detects the most likely task performed by the subject and therefore communicates the most adapted stimulation command to the IPG 12.

The baseline stimulation command is set by qualified person during a baseline parameterization session occurring after the INS implantation and is otherwise set to NULL by default.

There may be more than one baseline stimulation command. Such sets of stimulation commands may be directed and addressing situations like standing, lying and sitting, where for example no stimulation is needed.

In the embodiment, there are several sets of stimulation commands for specific kinds of safety modes designed to fit to the posture or orientation of the patient P.

Depending on a detected posture or orientation of the patient, e.g. detected and determined on the basis of signals from the sensor(s) 16, the regular mode or the safety mode will be automatically chosen by the pulse generating means 12 and the control unit 14. So, the safety mode is linked to the patient orientation as triggering event or condition, which is used to decide between regular mode or safety mode. The patient orientation, e.g. whether the patient is standing or lying or sitting or the like, is linked to a specific baseline command in the safety mode, i.e. there are different sets of baseline commands for specific kinds of safety modes designed to fit to the posture or orientation of the patient. This enhances the overall safety of the system in case that the patient changes from an active state, where the system is in the regular mode, like walking, tripping, falling to a resting state, where he is standing, lying or sitting and where the or one of the safety mode(s) is most suitable.

The system 10 can automatically switch from regular mode to safety mode if the control unit 14 determines the most adapted stimulation command is the current situation is baseline and the connection between the control unit 14 and the IPG 12 is lost.

Also, the patient P can decide to switch to safety mode.

The system 10 can automatically switch from safety mode to regular mode if the control unit 14 determines that the most adapted stimulation command is different from baseline, the lost connection between the control unit 14 and the IPG 12 is restored and the patient decides to switch to safety mode.

The pulse generating system 10 is capable of working in at least the regular mode and a safety mode.

In the regular mode the pulse generating means 12 and the controlling means 14 are connected.

In the safety mode there may be no connection between the pulse generating means 12 and the controlling means 14.

Also, in the safety mode the pulse generating means 12 automatically switches to a baseline stimulation command.

In the regular mode the controlling means 14 are capable and configured to control the pulse generating means 12 by providing control commands, especially control commands based on the input of the sensor 16.

The controlling means 14 is configured to control the pulse generating means 12 with a two-way information flow, i.e. that the controlling means 14 sends signals to the pulse generating means 12 and receives signals sent from the pulse generating means 14.

The controlling means 14 are be able to interact with the pulse generating means 12 such that it receives information and/or signals from the pulse generating means 12. Such information and/or signals may be used to influence the control commands provided by the controlling means 14.

Generally, it is also possible that the controlling means 14 may he configured to control the pulse generating means 12 with a one-way information flow, i.e. that the controlling means 14 only sends signals and/or control commands to the pulse generating means 12.

The baseline stimulation command for the safety mode is a default value set during a baseline parameterization session.

In particular, the baseline stimulation command for the safety mode may be also set to NULL by default.

By means of the automatic switching unit 18 it is possible to switch automatically from the regular mode to the safety mode and vice versa.

In particular the automatic switching unit 18 may switch automatically from regular mode to the safety mode, if a signal is received by the automatic switching unit 18, which indicates that the controlling means 14 have determined that the most adapted stimulation command to be provided by the pulse generating means 12 is the baseline command.

Moreover, the automatic switching unit 18 may be configured to switch automatically from regular mode to the safety mode, if a signal is received by the automatic switching unit 18, which indicates that the connection between the pulse generating means 12 and the controlling means 14 is lost.

Also, the automatic switching unit 18 may he configured to switch automatically from safety mode to the regular mode, if a signal is received by the automatic switching unit, which indicates that the controlling means 14 have determined that the most adapted stimulation command to he provided by the pulse generating means 12 is a command different from the baseline stimulation command.

Also by means of the automatic switching unit 18 it may automatically switch from safety mode to the regular mode, if a signal is received by the automatic switching unit 18, which indicates that the connection between the pulse generating means 12 and the controlling means 14 is restored after it was lost.

By means of the user input switching unit 20 it is possible for a user, i.e. the patient P or a physician or a nurse or any medical practitioner, to switch upon user input from a regular mode to the safety mode and vice versa. For example, the user input switching unit 20 may be an electronic module or unit contained within or electronically coupled to the control unit 14. The user input switching unit 20 may be adapted to receive a wired or wireless transmission from a remote, user input device. In this way, the user input switching unit 20 may receive control signals from a user for switching the system between the regular mode and safety mode.

The safety mode switching means 26 provide a further safety feature. The safety mode switching means 26 may be embodied as a part or integrated module of the or within the controlling means 14.

The safety mode switching means 26 may continuously control technical parameters of the overall system. Such a parameter may be low power or low battery power RF signal interferences, detected noise signal or disturbing signals, intermittent contact or connection between components of the system like the connection between the controlling means and/or the pulse generating means and/or the sensor.

If the safety mode switching means 26 receives an indication, e.g. by detection of abnormalities in the signals delivered to the controlling means 14, which is then detected by the safety mode switching means 26, then the safety mode switching means 26 switches the pulse generating system 10 automatically from regular mode to safety mode, triggered by detected abnormalities of technical system parameters.

The connection bridging means 28 can bridge the temporarily non-existing connection by replacing it with stored data, especially stored data obtained by simulation. If there is intermittent contact or connection between components of the system like the connection between the controlling means 14 and/or the pulse generating means 12 and/or the sensor 16.

The connection bridging means 28 bridge the temporarily non-existing connection by replacing it with stored data or signal data. Such data may be derived from or based on simulation data derived from comparable situations. In particular, sensor data may be simulated or taken from comparable situations and stored in a suitable simulation sensor data storage means. The sensor input, which is not available in case of an intermittent contact or connection between components of the system like the connection between the controlling means 14 and especially but not limited to the sensor 16 (also generally possible between controlling means 14 and the pulse generating means 12)

can then be replaced by the simulated sensor data in order to bridge the gap in the time frame, where there is no connection.

In particular, the overall system as shown in the figure is a system, in which the pulse generating means 12 delivers electrical stimulation to the subject spinal cord in order to enable or facilitate the initiation of limbs movement. The controlling means 14 receives sensor input on subject motion features and computes an optimal stimulation command to the given situation. Sensors 16 may include inter alia but not exclusively gyroscopes, accelerometers, video cameras, pressure sensors, force sensors, electromyograms (ENG), electro-encephalograms (EEG), neural probes, etc.

Motion features may include inter alia but not exclusively kinetics, kinematics, muscular activity, neuronal signals etc. Other targeted neuronal structures for other embodiments may include inter aha but not exclusively parts of the central nervous systems, parts of the peripheric nervous system, neuro-muscular junctions and body segments, etc.

Also, the implantable neurostimulation system may support biological functions related to movement, posture, proprioception, nociception, digestion, respiration, bladder control, bowel control etc.

The system as described above may be used for the rehabilitation of patients suffering from neurological disorders such as spinal cord injury (SCI) e.g. after trauma, stroke, multiple sclerosis, chronic pain, respiratory insufficiency, incontinence, etc.

Figure 2:
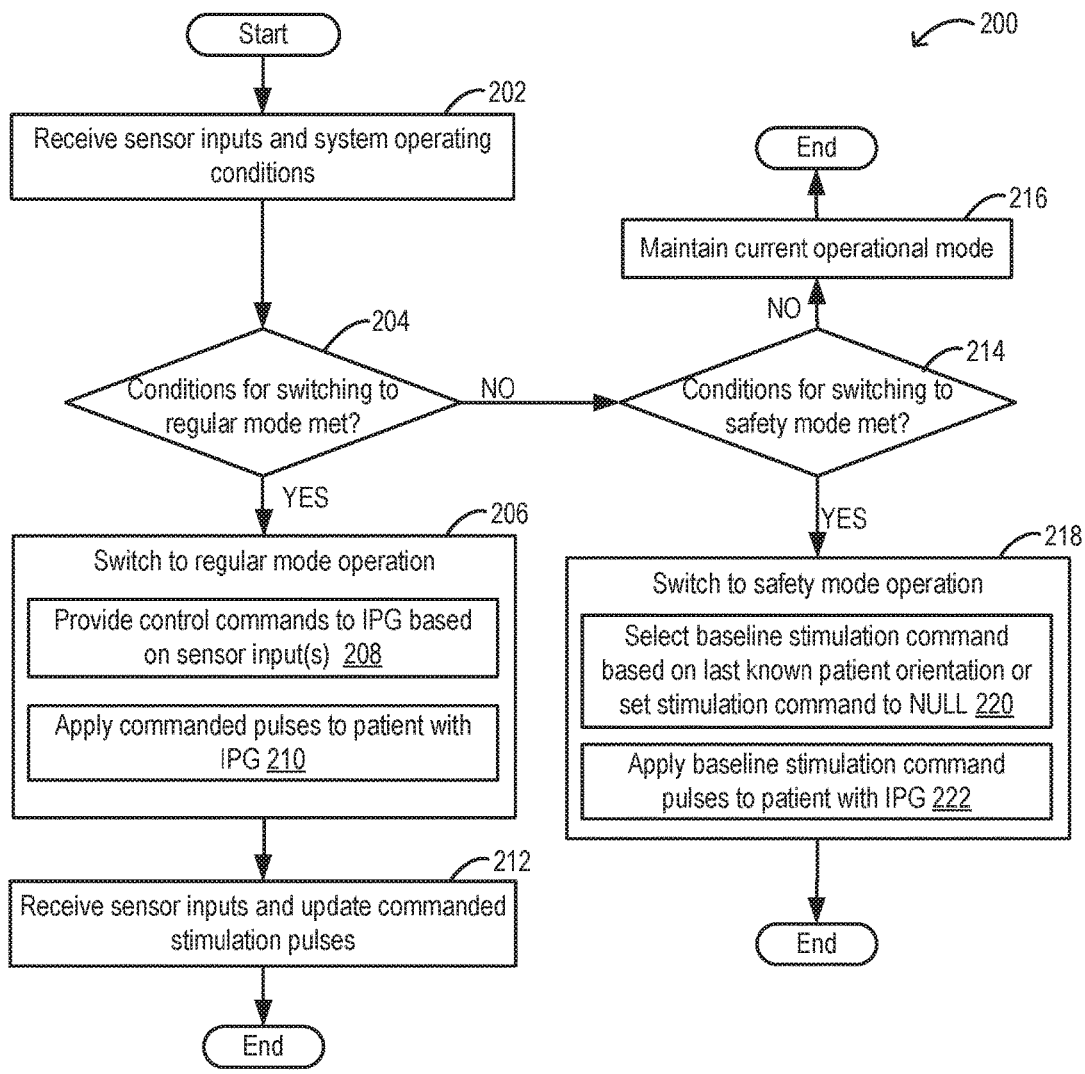
FIG. 2 shows a flow chart of a method for operating a pulse generating system of a closed loop neurostimulation system in different operational modes based on system signals and operating conditions.
Figure 3:
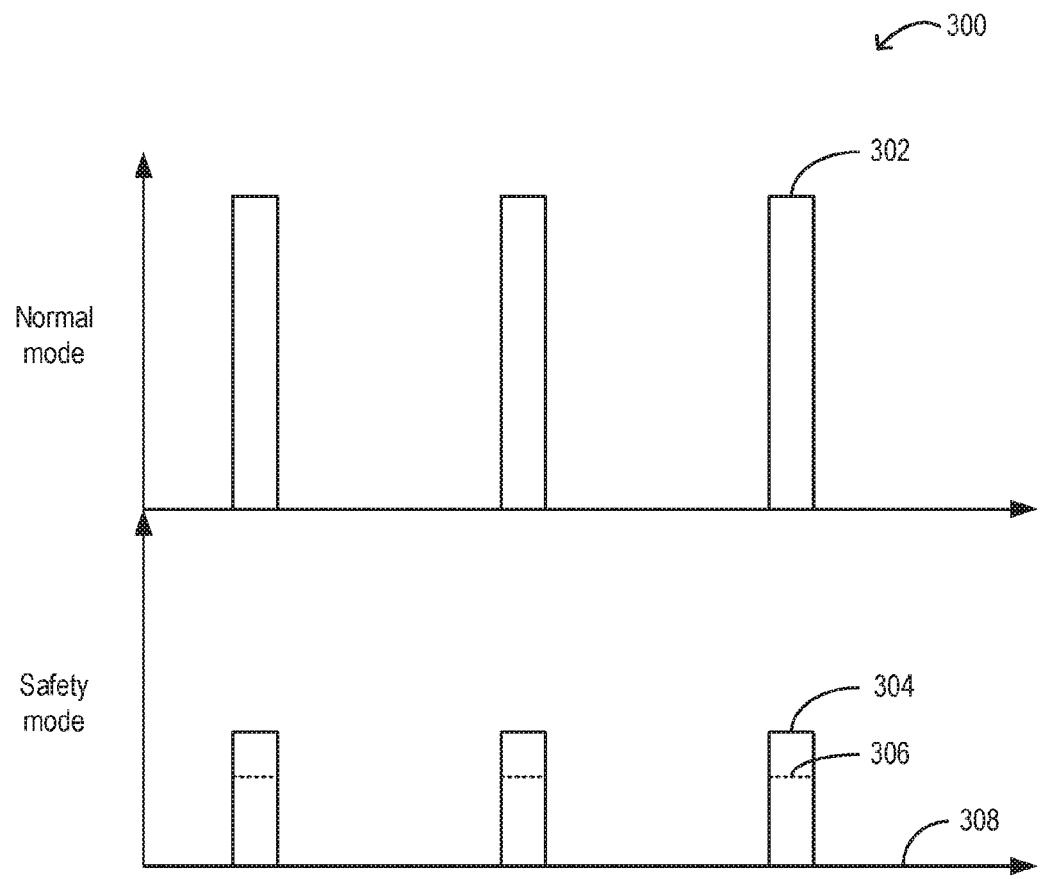
FIG. 3 shows a graph of example stimulation pulse commands applied to a patient via an implantable pulse generator during each of a normal mode and safety mode of operation.

FIG. 2 shows a method 200 for operating a pulse generating system of a closed loop neurostimulation system in different operational modes based on system signals and operating conditions. Method 200 may be executed by and according to instructions stored on memory of a control unit of the pulse generating system of the neurostimulation system, such as control unit 14 shown in FIG. 1 in conjunction with signals received from various sensors of the neurostimulation system, such as sensor 16 shown in FIG. 1.

Method 200 begins at 202 by receiving sensor inputs and system operating conditions of the neurostimulation system. In one example, the method at 202 may include receiving inputs from one or more sensors (such as sensor 16 shown in FIG. 1) coupled to a patient and in electronic communication (e.g., via a wireless connection) with the control unit. As explained above, the control unit may receive signals from the one or more sensors and then determine control signals (such as stimulation pulses) to send to the implantable pulse generator (IPG) implanted in the patient. In this way, the control signals may be adapted to a current situation (e.g., movement or position of the patient). The sensors may include gyroscopes, accelerometers, video cameras, pressure sensors, force sensors, electromyograms (EMO), electro-encephalograms (EEG), neural probes, etc. Additionally, the system operating conditions may include a power level of the pulse generating system (e.g., a power level of the control unit and/or the IPG), the presence or level of an electronic connection signal (wired or wireless) between the IPG and control unit, the presence or level of an electronic connection signal (wired or wireless) between the sensor(s) and the control unit, one or more inputs received at the control unit from a user, a low power battery RF signal, etc.

At 204, the method includes determining if conditions for switching to a regular mode from a safety mode are met. As described herein, the regular mode may include when the control unit and IPG are in electronic communication with one another and where the IPG delivers stimulation pulses to the patient (via the lead and electrodes coupled to the patient and connected to the IPG, as shown in FIG. 1) according to stimulation commands determined by the control unit and sent to the LPG from the control unit. As also described herein, the safety mode may include when the control unit and IPG are not in electronic communication with one another and thus the IPG may not receive stimulation commands from the control unit. As such, in the safety mode, the IPG may deliver a pre-determined, baseline stimulation pulse to the patient, or operate in a NULL mode where no pulses are delivered (e.g., applied) to the patient. Conditions for switching to the regular mode from the safety mode may include the patient changing from a stationary or resting position or orientation (e.g., such as standing, lying, or sitting) to a more active position or orientation (e.g., such as walking, tripping, or falling). Conditions for switching to the regular mode from the safety mode may additionally or alternately include the control unit receiving a signal from a user, via a user switching unit (such as user switching unit 20 shown in FIG. 1), indicating a desire to switch to the regular mode. Conditions for switching to the regular mode from the safety mode may additionally or alternately include if the control unit determines that the most adapted stimulation command is different from baseline and/or if the lost connection between the control unit and the IPG is restored (e.g., the control unit and IPG are communicatively coupled with one another such that the IPG may receive stimulation commands or control signals from the control unit).

If the conditions for switching to the regular mode are met, the method continues to 206 to switch operation of the pulse generating system from the safety mode to the regular mode. Switching to the regular mode at 206 may include, at 208, providing control commands (e.g., stimulation pulse values or commands) to the IPG from the control unit based on sensor inputs received at the control unit from the one or more sensors coupled to the patient, as described above. The method at 208 may include the control unit determining the desired stimulation pulse parameters to be delivered (applied) to the patient by the IGG, including one or more of a stimulation pulse level, pulse duration, pulse modulation frequency, which electrode (e.g., location of the lead) to activate to deliver the pulse, etc., based on one or more sensor inputs. In one example, the routine adjusts the stimulation pulses based on inputs or signals from the sensors coupled to the patient. For example, the control unit may determine a control signal to send to the IPG. such as a stimulation pulse value or duration based on data received from the sensors, which may include a position, orientation, movement, etc. of the patient. The control unit may determine the stimulation pulse command through a determination that directly takes into account the sensor inputs. The controller may alternatively determine the stimulation control commands based on a calculation using a look-up table with the input being the sensor inputs and the output being the stimulation pulse parameters or command signals. As another example, the control unit may make a logical determination (e.g., regarding a value of the stimulation pulse to be applied to the patient via the IPG) based on logic rules that are a function of inputs from the sensors coupled to the patient. The controller may then generate a control signal that is sent to the IPG.

The method at 210 then includes applying the determined commanded pulses (e.g., stimulation pulse parameters) to the patient with the IPG. At 212, the method includes receiving sensor inputs from the sensors coupled to the patient and updating the commanded stimulation pulses sent the IPG based on the received sensor inputs, as described above. The method then ends.

If the conditions for switching to the regular mode are not met, or the pulse generating system is already operating in the regular mode, the method continues to 214 to determine whether conditions for switching to the safety mode from the regular mode are met. Conditions for switching to the safety mode from the regular mode may include the patient changing from an active position or orientation (e.g., such as walking, tripping, or falling) to a stationary or resting position or orientation (e.g., such as standing, lying, or sitting). Conditions for switching to the safety mode from the regular mode may additionally or alternately include the control unit receiving a signal from a user, via the user switching unit (such as user switching unit 20 shown in FIG. 1), indicating a desire to switch to the safety mode. Conditions for switching to the safety mode from the regular mode may additionally or alternately include if the control unit determines that the most adapted stimulation command is the baseline stimulation command and/or if the connection (e.g., communicative or electronic connection) between the control unit and the IPG is lost or reduced to a level that is less than a threshold level, where the threshold level may be a level below which consistent or reliable commands may be received at the IPG from the control unit. Conditions for switching to the safety mode from the regular mode may additionally or alternately include a low power signal (e.g., power level below a threshold level), low battery power RF signal interferences, detected noise signal or disturbing signals, intermittent contact or connection between components of the system like the connection between the control and/or the IPG and/or the sensor.

If the conditions for switching to the safety mode are not met, or the system is already operating in the safety mode, the method continues to 216 to maintain operation of the pulse generating system in the current operational mode. Alternatively, if the conditions for switching to the safety mode are met, the method continues to 218 to switch operation of the pulse generating system from the regular mode to the safety mode. In the safety mode, the control unit may not be in communication with the IPG. At 220, the method includes selecting a baseline stimulation command (e.g., baseline stimulation level or stimulation pulse to be applied to the patient via the IPG and lead with electrodes). In one embodiment, the baseline stimulation command may be a set, pre-determined stimulation command that is stored and not adjusted during use of the IPG. In another embodiment, the baseline stimulation command may be a set level that is selected from a group of baseline stimulation commands based on the last known patient position or orientation. For example, if the patient was determined to be sitting before or upon entering the safety mode, the baseline stimulation command to use during the safety mode may be selected to be a first baseline stimulation command. However, if the patient was determined to be laying down before or upon entering the safety mode, the baseline stimulation command to use during the safety mode may be selected to be a second baseline stimulation command, different than the first baseline stimulation command. However, all the baseline stimulation commands may be pre-determined values or pulses that are stored at the IPG. In one example, all the baseline stimulation commands may be lower than a stimulation command used during the normal mode. In yet another embodiment, if the last known patient orientation is unknown or a baseline stimulation command is not stored or set at the IPG, the method at 220 may include setting the baseline stimulation command to NULL. At 222, the method includes applying the baseline stimulation command (e.g., pulses) to the patient with the IPG and associated lead. The method then ends.

FIG. 3 shows a graph of example stimulation pulse commands applied to a patient via the IPG during each of a normal mode and safety mode, as discussed herein. Specifically, graph 300 shows a first stimulation command (e.g., stimulation pulse) 302 applied via the IPG during the normal mode. The first stimulation command 302 may he adjusted based on signals received at the control unit from sensors positioned on the patient. Thus, the control unit may send the first stimulation command 302 to the IPG for application to the patient via the IPG lead(s). Graph 300 also shows a second stimulation command (e.g., stimulation pulse) 304 applied via the IPG during a safety mode when the patient is in a first orientation (e.g., sitting), a third stimulation command 306 applied via the IPG during the safety mode when the patient is in a second orientation (e.g., laving down), and a fourth stimulation command 308 which may be a NULL command in the safety mode, The second stimulation command 304 and third stimulation command 306 are both set, pre-determined levels that are selected based on the patient orientation or position just prior to or upon entering the safety mode from the normal mode of operation of the pulse generating system. Both of these stimulation commands may be at lower levels than the first stimulation command 302 while operating in the normal mode. In this way, lower level pulses may be delivered to the patient via the IPG during the safety mode when the IPO may not be in electronic communication with the control unit.

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with the electronic control unit.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A pulse generating system, comprising:
a pulse generator adapted to generate a pulse or pulses; and
a controller designed to be continuously connected to the pulse generator and adapted to control the pulse generator, wherein the pulse generating system is adapted to operate in at least a regular mode and a safety mode, wherein in the regular mode the pulse generator and the controller are connected and wherein in the safety mode there is no or limited connection between the pulse generator and the controller and wherein in the safety mode the pulse generator automatically switches to a baseline stimulation command, wherein the controller is connected with one or more sensors and forms a closed-loop system together with the one or more sensors.

2. The pulse generating system according to claim 1, wherein each of the controller, the pulse generator, and the one or more sensors are adapted to be attached to or implanted within a patient.

3. The pulse generating system according to claim 2, wherein in the regular mode the controller is configured to control the pulse generator by providing control commands, where the control commands are based on a sensor input by at least one sensor of the one or more sensors and wherein the pulse generator and the controller are separated from each other.

4. The pulse generating system according to claim 1, wherein the controller is adapted to communicate with the pulse generator one-way by sending control signals only.

5. The pulse generating system according to claim 1, wherein the controller is adapted to communicate with the pulse generator two-way by sending and receiving control signals and signals and wherein the baseline stimulation command for the safety mode is selected based on a last known patient orientation of a patient to which the pulse generating system is coupled.

6. The pulse generating system according to claim 1, wherein the baseline stimulation command for the safety mode is a default value set during a baseline parameterization session.

7. The pulse generating system according to claim 1, wherein the baseline stimulation command for the safety mode is set NULL by default.

8. The pulse generating system according to claim 1, wherein the pulse generating system further comprises an automatic switching unit, wherein the automatic switching unit is an electronic module contained within the controller, configured to switch automatically from the regular mode to the safety mode and vice versa.

9. The pulse generating system according to claim 8, wherein the automatic switching unit is configured to switch automatically from the regular mode to the safety mode, if a signal is received by the automatic switching unit which indicates that the controller has determined that the most adapted stimulation command to be provided by the pulse generator is the baseline stimulation command.

10. The pulse generating system according to claim 8, wherein the automatic switching unit is configured to switch automatically from the regular mode to the safety mode, if a signal is received by the automatic switching unit which indicates that the connection between the pulse generator and the controller is lost or reduced to a level below a threshold level.

11. The pulse generating system according to claim 8, wherein the automatic switching unit is configured to switch automatically from the safety mode to the regular mode, if a signal is received by the automatic switching unit which indicates that the controller has determined that the most adapted stimulation command to be provided by the pulse generator is a command different from the baseline stimulation command.

12. The pulse generating system according to claim 8, wherein the automatic switching unit is configured to switch automatically from the safety mode to the regular mode, if a signal is received by the automatic switching unit which indicates that the connection between the pulse generator and the controller is restored after it was lost or reduced.

13. The pulse generating system according to claim 1, wherein the pulse generating system further comprises a user input switching unit to switch, upon user input, from the regular mode to the safety mode and vice versa and wherein the baseline stimulation command is less than a stimulation command provided during the regular mode but greater than a NULL command.

14. The pulse generating system according to claim 1, wherein the pulse generating system further comprises a safety mode switching switch, which is configured switch the pulse generating system automatically from the regular mode to the safety mode when triggered by technical system parameters.

15. The pulse generating system according to claim 1, wherein the pulse generating system further comprises a connection bridge, which is configured to bridge the no or limited connection by replacing it with stored data, including stored data obtained by simulation.

16. A method for controlling a pulse generating system, comprising:
automatically switching between a regular mode where a controller and implantable pulse generator (IPG) of the pulse generating system are communicatively coupled with one another and the IPG provides stimulation pulses to a patient as commanded by the controller and a safety mode where the controller and the IPG are not communicatively coupled with one another and the IPG provides a baseline stimulation pulse to the patient, where the baseline stimulation pulse is pre-set and not commanded by the controller, in response to one or more conditions for switching modes, including a change in one or more of a communicative connection between the controller and the IPG, an orientation of the patient, and a power signal of the pulse generating system, wherein the controller determines the commanded stimulation pulses based on inputs from one or more sensors of the pulse generating system that are positioned on the patient and sends the determined commanded stimulation pulses to the IPG, and wherein operation in the regular mode and the communicative coupling between the controller and the IPG is maintained until one or more of the conditions for switching modes is met.

17. The method of claim 16, wherein the controller is attached to the patient and the IPG is implanted within the patient.

18. The method of claim 16, further comprising switching from the regular mode to the safety mode in response to one or more of losing the communicative connection, the change in orientation being a change in orientation from an active position to a resting position, and a low power signal of the pulse generating system.

19. The method of claim 16, further comprising switching from the safety mode to the regular mode in response to one or more of restoring the communicative connection and the change in orientation being a change in orientation from a resting position to an active position.

20. A pulse generating system, comprising:
an implantable pulse generator implanted in a patient and configured to deliver stimulation pulses to the patient via a lead containing one or more electrodes coupled to the patient;
at least one sensor positioned on the patient; and
a controller positioned on the patient and in electronic communication with each of the at least one sensor and the implantable pulse generator, the controller designed to be in continuous electronic communication with the controller, the controller including instructions stored in memory for:
determining a stimulation pulse based on an input received from the sensor;
commanding the implantable pulse generator, via sending a control signal to the implantable pulse generator, to apply the determined stimulation pulse to the patient; and
switching to applying a pre-determined, baseline stimulation pulse to the patient with the implantable pulse generator in response to one or more of losing the electronic communication between the controller and the implantable pulse generator and a lower power signal of the pulse generating system.

* * * * *